United States Patent [19]

Amundsen et al.

[11] 4,271,085
[45] Jun. 2, 1981

[54] CIS-PLATINUM (II) AMINE LACTATE COMPLEXES

[75] Inventors: Alan R. Amundsen, Somerville; Eric W. Stern, Mountainside, both of N.J.

[73] Assignee: Engelhard Minerals & Chemicals Corporation, Iselin, N.J.

[21] Appl. No.: 50,235

[22] Filed: Jun. 20, 1979

[51] Int. Cl.$^3$ ............................................. C07F 15/00
[52] U.S. Cl. ................................. 260/429 R; 424/287
[58] Field of Search .................................... 260/429 R

[56] References Cited

U.S. PATENT DOCUMENTS

| 4,115,418 | 9/1978 | Gale et al. | 260/429 R |
| 4,140,707 | 2/1979 | Cleare et al. | 260/429 R |

OTHER PUBLICATIONS

Ridgway et al., J. of Clinical Hemotology and Oncology, 7, No. 1, p. 220, (1976).
Cleare et al., Bioinorganic Chemistry, V2, pp. 187–210, (1973).
Speer et al., J. of Clinical Hemotology and Oncology, 7 (3), p. 856, (1977).
Schwartz et al., Cancer Treatment Reports, V61 (8), pp. 1519–1525, (1977).
Marx, Science vol. 192 (424), pp. 774–775, (1976).
Cleare, Coordination Chemistry Reviews, vol. 12, pp. 349–404, (1974).
Connors et al., Platinum Coordination Complexes in Cancer Chemotherapy, Springer Verlag, N.Y., pp. 1–199, (1974).

*Primary Examiner*—Helen M. S. Sneed

[57] ABSTRACT

Cis-Platinum(II) amine lactate complexes are prepared by reaction of the appropriate platinum(II) amine chloride complex with silver lactate. These complexes possess pronounced anti-tumor activity and low toxicity and thus have high therapeutic indices. They are also highly soluble in water.

7 Claims, 6 Drawing Figures

IR Spectrum of [Pt(CH$_3$NH$_2$)$_2$(Lactate)$_2$]

IR Spectrum of [Pt(en)(Lactate)$_2$]

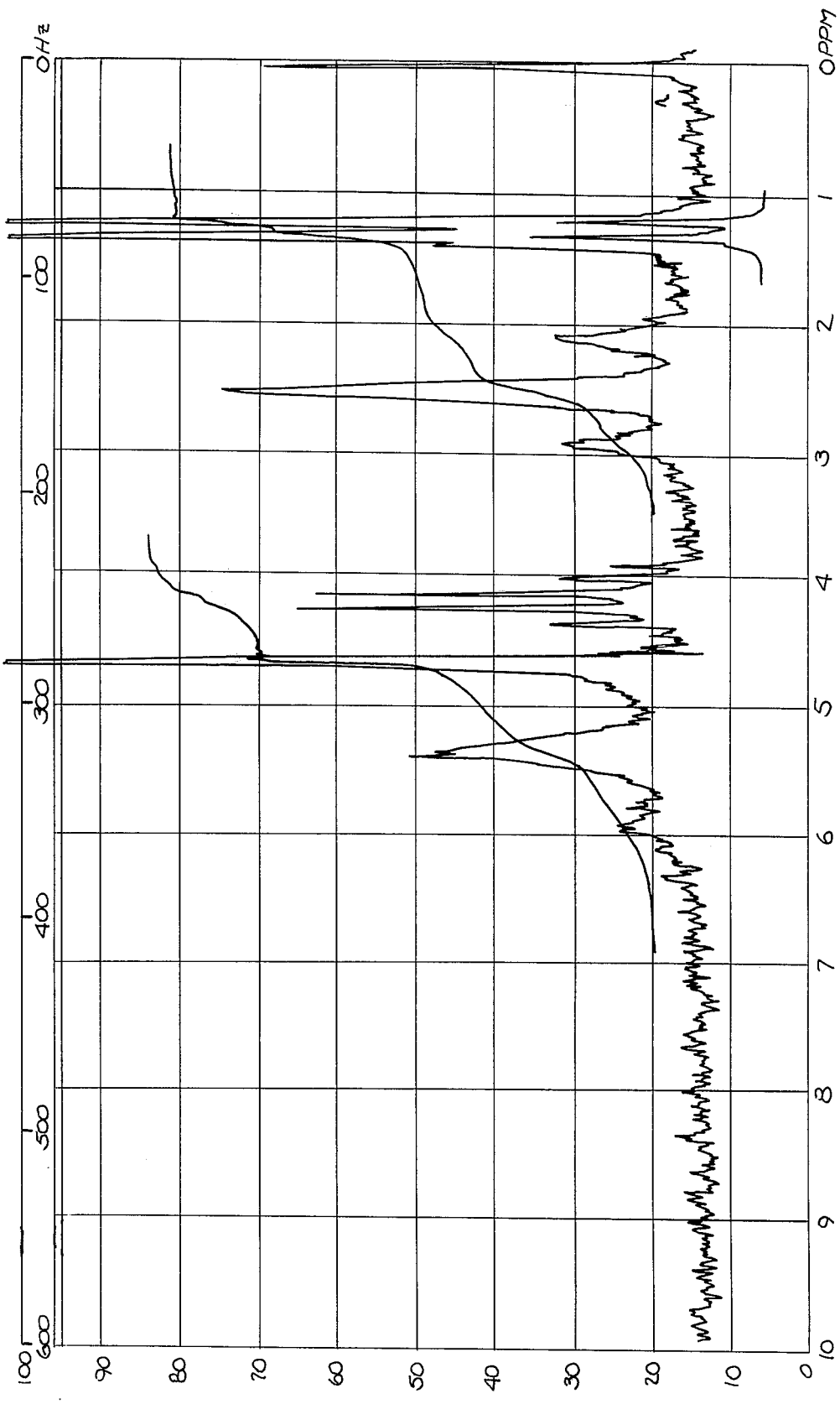
FIG. 5. NMR Spectrum of [Pt(en)(Lactate)₂]

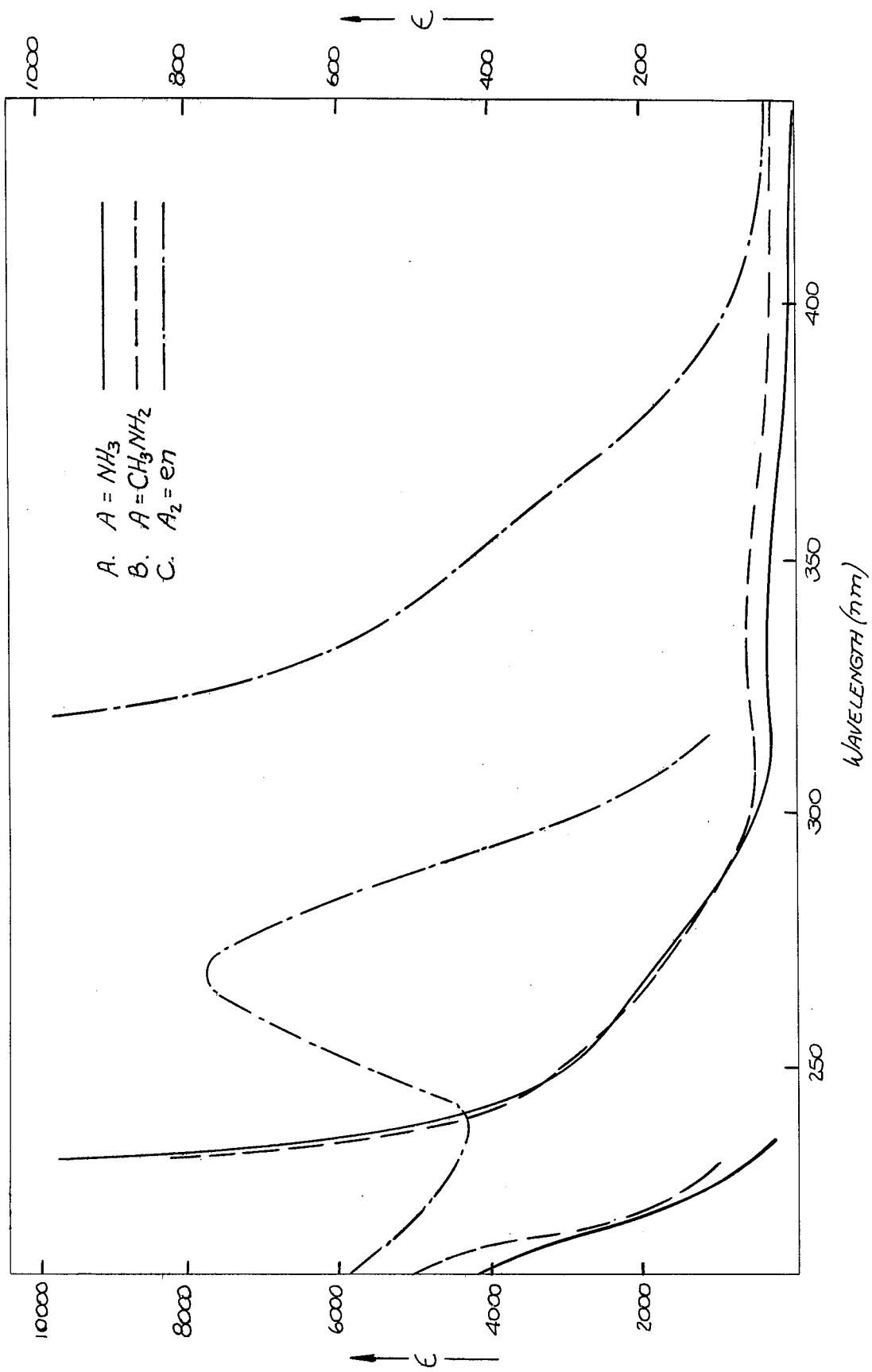

CIS-PLATINUM (II) AMINE LACTATE COMPLEXES

This invention is concerned with certain lactate complexes of platinum(II). More particularly, this invention is concerned with cis-platinum(II) amine lactate complexes where the amine moiety is ammonia, an alkylamine or a bidentate alkylenediamine. These compounds have the general formula cis-[PtA$_2$(lactate)$_2$], where A is ammonia or an alkyl amine such as methylamine and A$_2$ is a bidentate alkylenediamine moiety such as ethylenediamine. These compounds are characterized by being highly water soluble and possessing pronounced activity against tumors but low animal toxicity.

BRIEF DESCRIPTION OF THE DRAWINGS

FIG. 5 is a reproduction of the nuclear magnetic resonance spectrum of ethylenediamine cis-platinum(II) lactate complex of Example 3.

FIG. 6 is a reproduction of the ultraviolet spectra of the three compounds.

BACKGROUND

Figure 1:
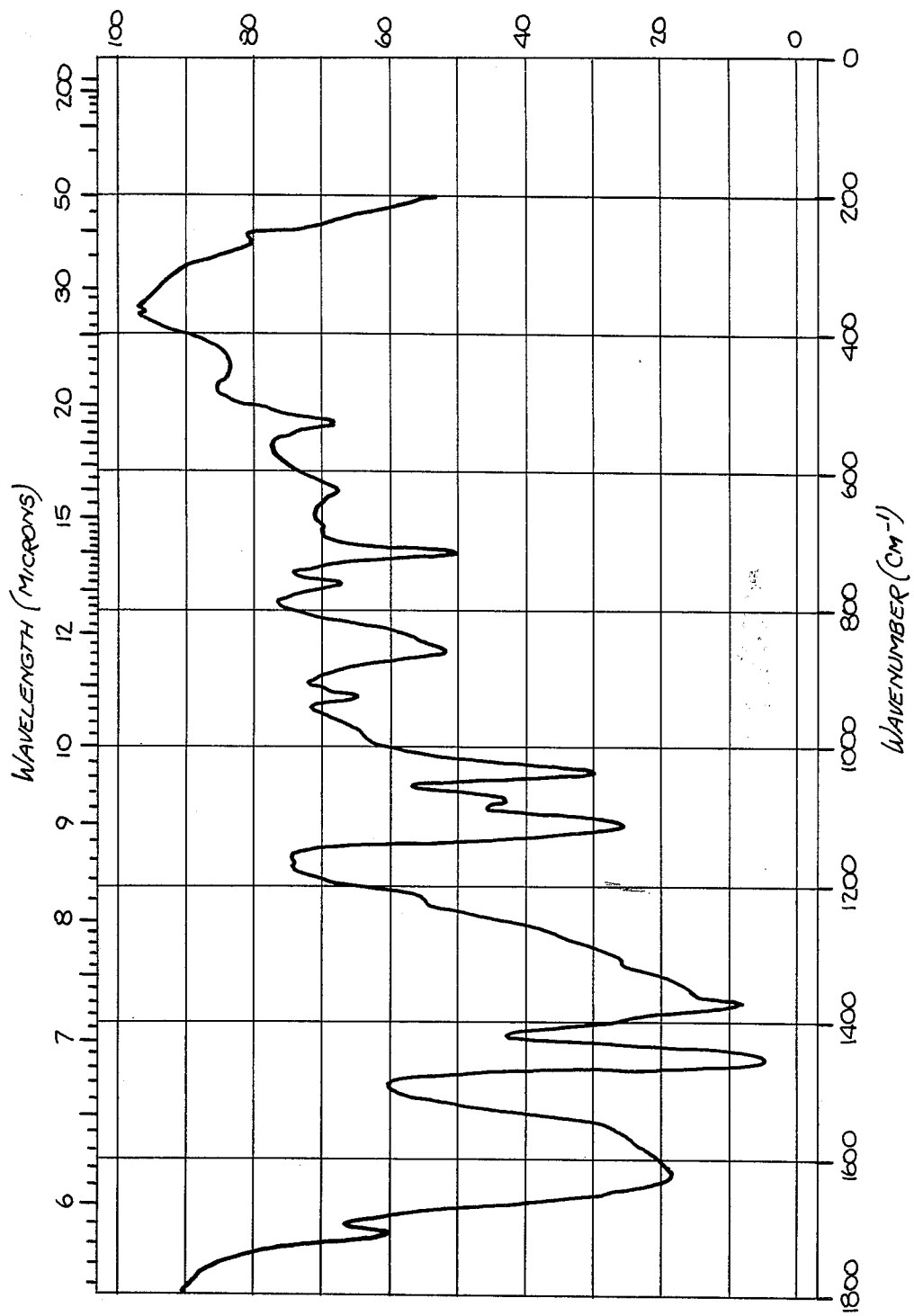
FIG. 1 is a reproduction of the infrared spectrum of the diammine cis-platinum(II) lactate complex of Example 1.

Rosenberg and Van Camp reported the discovery that certain platinum coordination compounds are of interest as potential anti-tumor agents. (Rosenberg and Van Camp, "Platinum Compounds: A New Class of Potential Anti-Tumor Agents", Nature, 222, 385–86 (1969)). This discovery has led to extensive testing of platinum and other transition metal compounds for similar activity. See, e.g., M. J. Cleare, "Transition Metal Complexes in Cancer Therapy", Coordination Chemistry Reviews, 12, 349–405 (1974). A platinum lactate complex containing 1,2-diaminocyclohexane has been reported to show activity vs. L1210 leukemia in mice. (Ridgway et al., "Analogs of Sulfato 1,2-Diaminocyclohexane Platinum (II). -I. Modifications in leaving Ligand", Journal of Clinical Hematology and Oncology, 7, No. 1, 220 (1976), and Speer et al., "Analogs of Malonato 1,2-Diaminocyclohexane Platinum (II) as Potential Anti-Tumor Agents", Journal of Clinical Hematology and Oncology, 7, No. 3, 856 (1977)). The cis-[PtA$_2$X$_2$] (A=amine, X=anion) species which have provided anti-tumor activity are not as a class very soluble. See, e.g., J. L. Marx, Science, 192, 774 (1976). Solubilities observed (in water or saline at 37° C.) range from 0.04 g/100 ml for cis-[Pt(NH$_3$)$_2$(malonate)] to 1.38 g/100 ml for cis-[Pt(CH$_3$NH$_2$)$_2$Cl$_2$]. (Cleare and Hoeschele, Bioinorganic Chemistry, 2, 187 (1973)). Low water solubility greatly reduces the compounds' utility for oral or intravenous administration. The novel lactate complexes of the present invention are highly soluble in water (greater than 10 g/100 ml when freshly prepared) and would overcome this problem.

SUMMARY OF THE INVENTION

In accordance with the present invention, there are provided novel lactate complexes of platinum(II) coordinated to two monodentate amine moieties or one bidentate amine moiety. These compounds are highly soluble; when freshly prepared they are soluble in water at room temperature to the extent of greater than 10 g per 100 ml. All of the compounds show excellent anti-tumor activity in mice and in addition, they have low mammalian toxicity. As a consequence, the complexes of this invention have more favorable therapeutic indices than previously known anti-neoplastic platinum (II) complexes.

The platinum(II) complexes of the invention may be represented by the general formula:

cis-[Pt(II)A$_2$(C$_3$H$_5$O$_3$)$_2$]

wherein A is ammonia (NH$_3$) or a monodentate alkylamine represented by the formula RNH$_2$ and R is hydrogen or lower alyl, or wherein A$_2$ is a bidentate diamine moiety represented by the general formula:

$$\overset{R^1}{\underset{|}{}} \;\; \overset{R^2}{\underset{|}{}}$$
$$H_2N-CH-CH-NH_2$$

wherein each of R$^1$ and R$^2$, when taken separately, is hydrogen or lower alkyl. By the term "Lower alkyl", as employed herein, is meant a linear or branched chain alkyl group of from 1 to about 6 carbons, and preferably from 1 to about 3 carbons. Illustrative amines include methylamine, ethylamine, propylamine, isopropylamine, ethylenediamine, 1,2-propylenediamine and the like. The preferred diamine is ethylenediamine.

The lactate moiety, (C$_3$H$_5$O$_3$), has the following optically active isomeric structures:

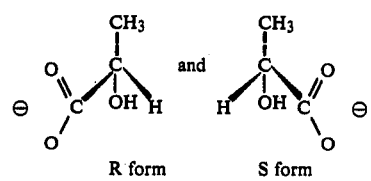

R form      S form wherein ⟶ signifies that the attached group is above the plane of the paper and --- signifies that the attached group is below the plane of the paper. The lactate moiety of the complex [PtA$_2$(C$_3$H$_5$O$_3$)$_2$] can be derived from either of the optically active lactate isomers, or a racemic mixture of both.

The complexes of this invention are prepared by reacting the corresponding amine complexed diaquo-cis-platinum(II) salt with a lactate salt in aqueous medium.

The "diaquo" salt is represented by the formula:

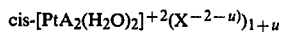

cis-[PtA$_2$(H$_2$O)$_2$]$^{+2}$(X$^{-2-u}$)$_{1+u}$ wherein A$_2$ is as defined above, X is an inorganic anion and u is 0 or 1. Suitable anions are those which are stable in acid media; they include sulfate, nitrate, and perchlorate, although nitrate is preferred. Anions having a greater complexing ability than water or lactate, such as chloride, bromide and iodide are not suitable.

The "diaquo" salt is formed from the stoichiometric reaction of the dichloro-cis-platinum amine complex with a silver salt, preferably silver nitrate, in an aqueous medium at room temperature. Although room temperature is preferred for the reaction, higher or lower temperatures may be employed, e.g., from about 0° C. to about 50° C. The "diaquo" salt is unstable in solution, but may be converted to stable solid cis-$[PtA_2(OH)]_2\cdot(NO_3)_2$ by reaction with one gram mole of base per gram atom of platinum. The dimeric complex may be reconverted to a monomer with acid or used directly in the preparation of the lactate compounds.

The lactate salts which are eployed are water soluble salts, preferably alkali metal lactate salts such as sodium or potassium lactate. The diaquo salt solution is then reacted with the lactate salt in an aqueous medium, preferably in a stoichiometric ratio, i.e., about 2 moles of lactate ion per gram atom of platinum. A ratio of from about 1.8 to about 2.2 equivalents of lactate per gram atom of platinum is generally useful. The concentration of the reactants in the aqueous medium is not highly critical; however, it is preferred that the reaction medium by approximately 0.2 molar, i.e., from about 0.1 to about 0.3 molar, with respect to platinum. The mixture is stirred at ambient temperature for a period of time sufficient to form the compounds of this invention. If desired, temperatures above or below ambient temperature, e.g., from about 0° C. to 50° C., may be employed. The period of reaction can vary with the conditions from minutes to several hours. However, the high water solubility of cis-$[PtA_2(C_3H_5O_3)_2]$ coupled with the low affinity of Pt(II) for monodentate carboxylates makes it difficult to isolate cis-$[PtA_2(C_3H_5O_3)_2]$ from this reaction mixture.

The complexes of this invention may also be prepared from cis-$[PtA_2Cl_2]$ by direct reaction in aqueous or alcoholic medium with a metal lactate salt, e.g., silver lactate, resulting in silver chloride which is not soluble in water.

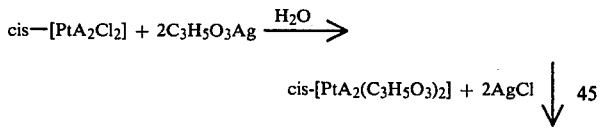

The metal lactate salt is present in the reaction mixture in a stoichiometric ratio, i.e., 2 moles of lactate salt to one mole of cis-platinum amine chloride. The reaction medium is aqueous or alcoholic preferably methanolic or ethanolic. The mixture is stirred at ambient temperature for a period of time sufficient to form the compounds of this invention. Higher or lower temperatures may be used, i.e., about 0° C. to about 70° C. When the reaction is carried out in methanolic medium, the reaction mixture is heated to about 60° C. and stirred for about an hour; after which, the mixture is cooled to ambient temperature. Then the metal chloride may be removed from solution by centrifugation or filtration. The filtrate is evaporated to dryness preferably at room temperature. If desired, the thus recovered cis-$[PtA_2(C_3H_5O_3)_2]$ may be recrystallized from a mixture of water, ethanol and acetone. When A is $NH_3$, this second procedure is preferably conducted in an alcoholic solvent in which cis-$[PtA_2(C_3H_5O_3)_2]$ is soluble, e.g., methanol. The alcoholic solvent is evaporated off preferably under vacuum. The residue is then recrystallized from an alcohol-acetone mixture. The procedure takes less time and a higher yield is obtained.

The complexes of this invention are expecially useful in tumor chemotherapy, having been found active against Sarcoma 180 ascites (S180a) in mice. The compounds were injected as aqueous solutions. The dosage level required for anti-tumor activity is not narrowly critical. The range of maximum activity was from 15 mg/kg to 120 mg/kg and about one fourth of the toxic dose in cases where toxic doses are reached. This represents a clear improvement over cis-$[Pt(NH_3)_2Cl_2]$ for which maximum activity occurs at around 8–10 mg/kg, about one half of the toxic dose of 16 mg/kg. The results indicate improved therapeutic indices for these compounds.

The following examples are illustrative. In the examples, the symbol "en" designates the ethylenediamine moiety.

EXAMPLE 1

Synthesis of cis-diammineplatinum(II) lactate, cis-$[Pt(NH_3)_2(C_3H_5O_2)]$ (a) Cis-$[Pt(NH_3)_2Cl_2]$ (1.5 g) was suspended in water (100 ml) and to it was added a suspension of silver lactate (2.15 g; Ag/Pt=2:1) in water (20 ml). The mixture was stirred at room temperature for 24 hrs. while protected from light. Silver chloride was removed by filtration and washed with water. Filtrate and washings were evaporated to dryness preferably under vacuum at room temperature, leaving a light yellow oil. This was dissolved in a water (7 ml) and ethanol (90 ml) mixture and then acetone (150 ml) was added intermittently while storing the solution in a freezer. After one week the white solid which had formed was filtered, washed with cold ethanol, and vacuum dried at room temperature. Yield was 0.74 g (36.4%).

Analysis: cis-$[Pt(NH_3)_2(C_3H_5O_3)_2]$ Calculated: C, 17.69%, H, 3.93%; N, 6.87% Found: C, 17.37%; H, 3.30%; N, 6.94%

(b) Cis-$[Pt(NH_3)_2Cl_2]$ (0.3 g) was suspended in methanol (25 ml) and solid silver lactate (0.43 g; Ag/Pt=2:1) added directly. The mixture was warmed to 60° C., then allowed to cool while stirring for one hour. The silver chloride was filtered off, washed with methanol, and the filtrate and washings evaporated to dryness on a rotary evaporator. The residue was dissolved in about 10 ml of methanol and then acetone was added until the solution was cloudy. It was stored in a freezer overnight. The white solid product was filtered, washed with acetone, and vacuum dried. Yield was 0.29 g (71.4%).

Analysis: cis-$[Pt(NH_3)_2(C_3H_5O_3)_2]$ Calculated: C, 17.69%; H, 3.93%; N, 6.87%; Found: C, 18.93%; H, 3.59%; N, 6.61%.

The infrared spectrum for this complex is reproduced in FIG. 1. The assignments are tabulated in Table I. The ultraviolet spectrum is reproduced as curve A in FIG. 6.

EXAMPLE 2

Synthesis of cis-bis(methylamine)platinum(II) lactate, cis-$[Pt(CH_3NH_2)_2(C_3H_5O_3)_2]$ Cis-$[Pt(CH_3NH_2)_2Cl_2]$ (1.065 g) was suspended in water and solid silver lactate (1.396 g; Ag/Pt=2:1) added directly. After stirring overnight while protected from light, the silver chloride was filtered off and washed with water. The filtrate and washings were evaporated to dryness under vacuum at room temperature, leaving a glassy residue. This was dissolved in ethanol (15 ml) and actone (25 ml) added, and the mixture stored in a freezer overnight. The white solid product was filtered, washed with acetone and ether and vacuum dried. Yield was 0.81 g (57.4%). The product is hygroscopic and will decompose when exposed to light. Therefore, the compound should be stored in a desiccator protected from light.

Analysis: cis-[Pt(CH$_3$NH$_2$)$_2$(C$_3$H$_5$O$_3$)$_2$] Calculated: C, 22.07%; H, 4.63%; N, 6.43%; Found: C, 22.26%; H, 3.98%; N, 6.33%.

Figure 2:
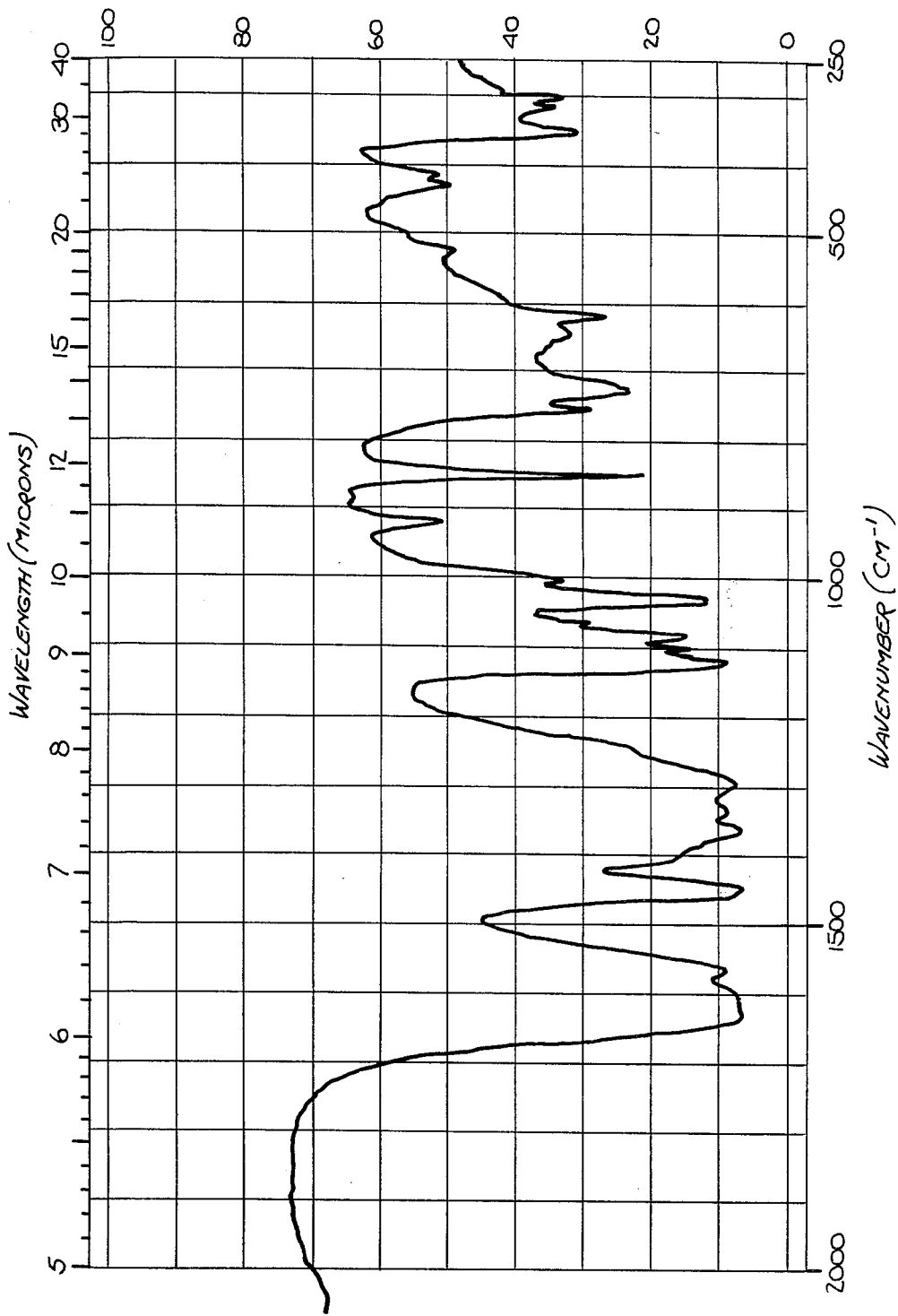
FIG. 2 is a reproduction of the infrared spectrum of the bis-(methylamine)cis-platinum(II) lactate complex of Example 2.
Figure 3:
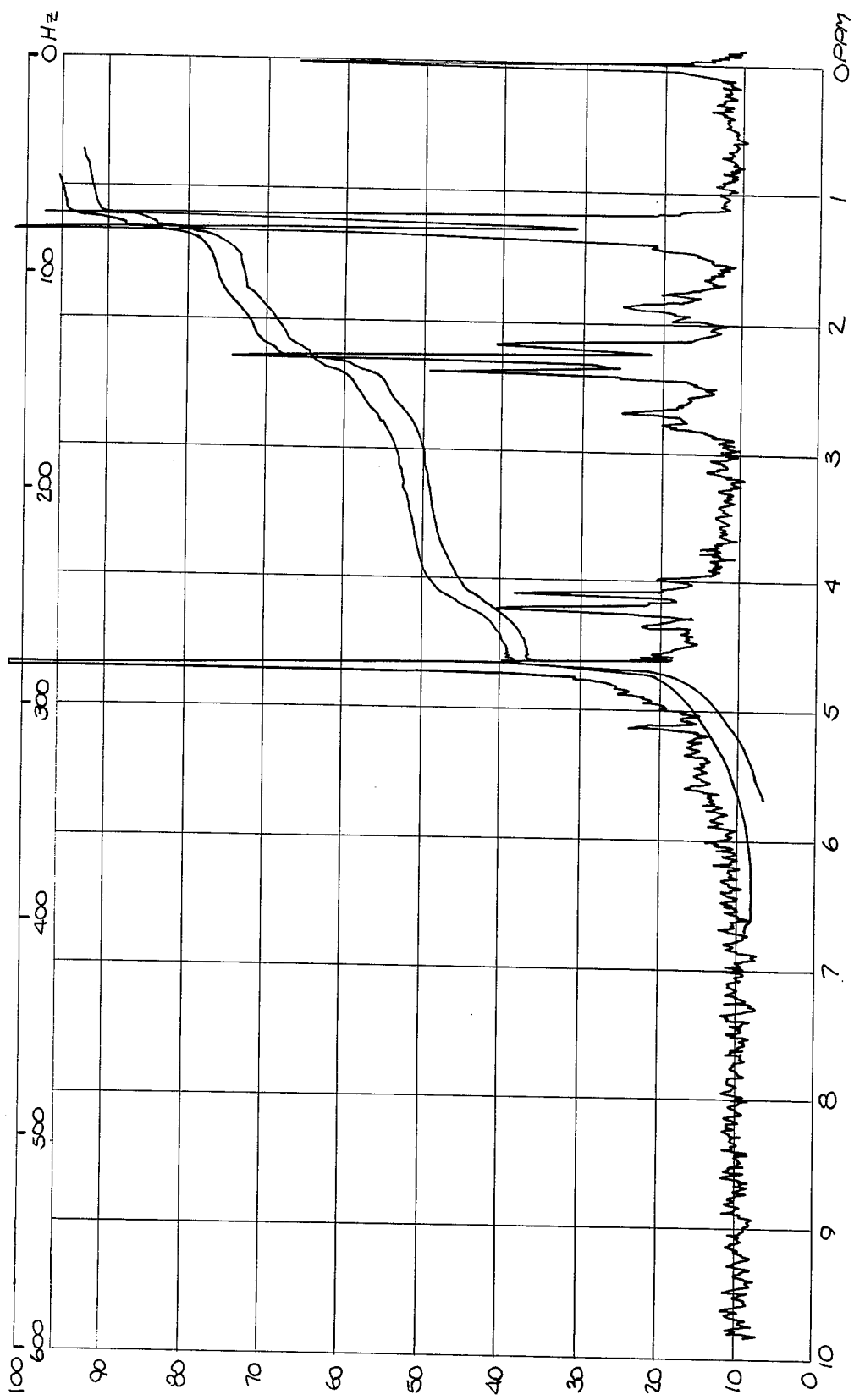
FIG. 3 is a reproduction of the nuclear magnetic resonance spectrum of bis-(methylamine)cis-platinum-(II) lactate complex of Example 2.

The infrared spectrum is reproduced in FIG. 2 and the band assignments are tabulated in Table I. The nuclear magnetic resonance spectrum is reproduced in FIG. 3. The ultraviolet spectrum is reproduced as curve B in FIG. 6.

EXAMPLE 3

Synthesis of Ethylenediamineplatinum(II) lactate, [Pt(en)(C$_3$H$_5$O$_3$)$_2$]

[Pt(en)Cl$_2$] (3.26 g) was suspended in water and silver lactate (4.3 g; Ag/Pt=2:1) added. After stirring overnight while protected from light, silver chloride was filtered off and the filtrate evaporated to dryness under vacuum at room temperature. The residue was dissolved in water, filtered to remove insoluble impurities, and ethanol (10 ml) and acetone (55 ml) added intermittently while cooling in a freezer for about 5 days. The white crystalline product was filtered, washed with acetone, and dried under vacuum. Yield was 3.17 g (73.2%). The product decomposes slowly when exposed to light and should be protected from light when stored.

Analysis: [Pt(C$_2$H$_8$N$_2$) (C$_3$H$_5$O$_3$)$_2$] Calculated: C, 22.17%; H, 4.19%; N, 6.46%; Found: C, 22.17%; H, 3.49%; N, 6.05%.

Figure 4:
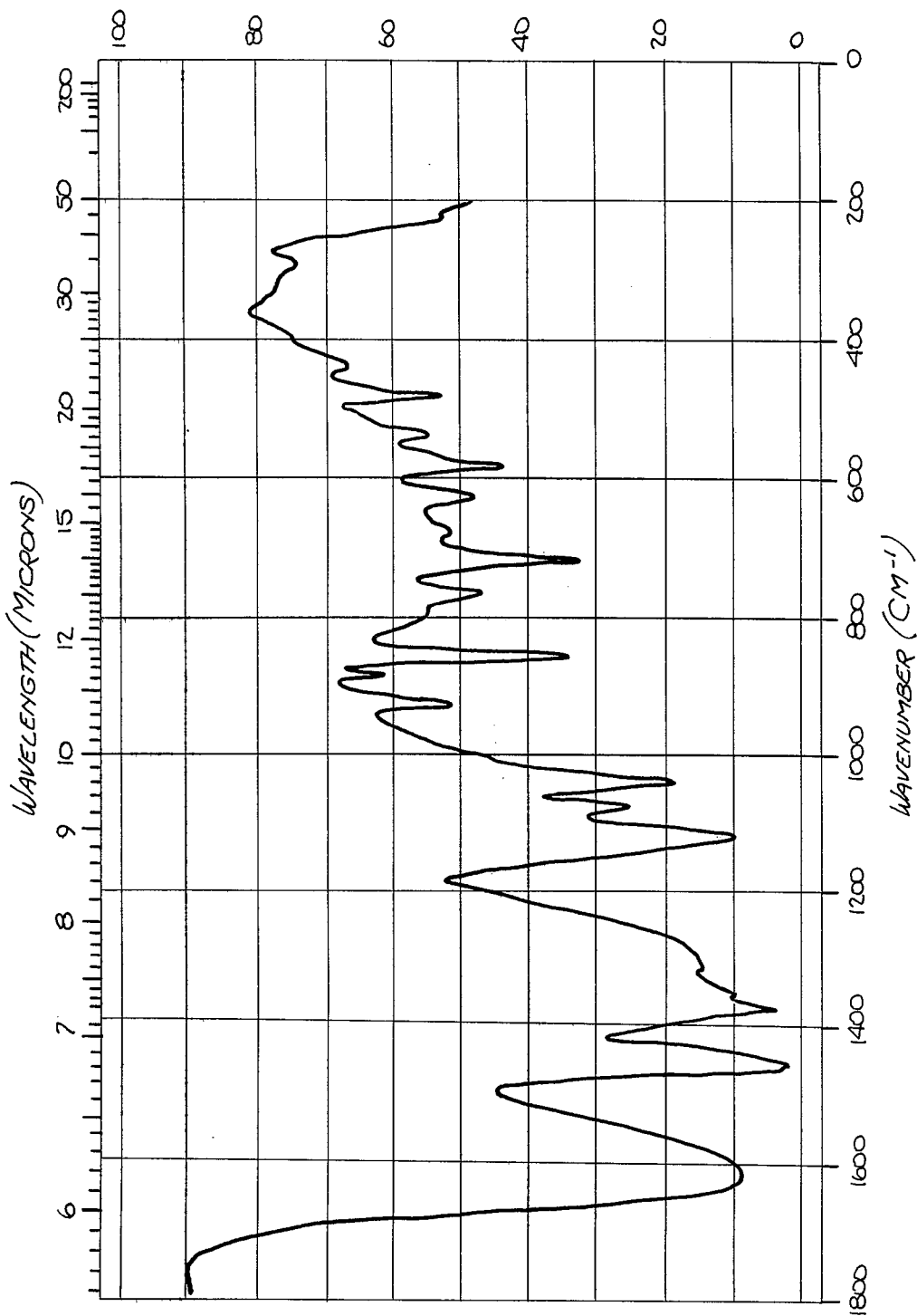
FIG. 4 is a reproduction of the infrared spectrum of the ethylenediamine cis-platinum(II) lactate complex of Example 3.

The infrared spectrum is reproduced in FIG. 4 and the band assignments are tabulated in Table I. The nuclear magnetic resonance spectrum is reproduced in FIG. 5. The ultraviolet spectrum is reproduced as curve C in FIG. 6.

TABLE I

Major Infrared Absorbances of cis-[PtA$_2$(C$_3$H$_5$O$_3$)$_2$] Complexes[a]

| Pt(NH$_3$)$_2$(C$_3$H$_5$O$_3$)$_2$ (Example 1) | Pt(CH$_3$NH$_2$)$_2$(C$_3$H$_5$O$_3$)$_2$ (Example 2) | Pt(en)(C$_3$H$_5$O$_3$)$_2$ (Example 3) | Assignment |
|---|---|---|---|
| 3400 sh | 3400 s | 3380 sh | $\nu$OH |
| 3260 s | 3350 sh | 3200 s | $\nu$NH |
| 3170 sh | 3230 s | 3120 sh | |
| 1710 m | | | $\nu$CO$_2$(assym) |
| 1620 s | 1630 s | 1610 s | $\delta$NH$_2$ |
| 1570 sh | 1600 sh | | |
| 1350 sh | 1335 s | 1350 sh | $\nu$CO$_2$-(sym) |
| 1310 sh | 1290 sh | 1300 sh | $\delta$NH$_2$ |
| 1220 sh | 1240 sh | | |
| 1110 s | 1120 s | 1110 s | Lactate |
| | 1100 m | | |
| 1075 m | 1070 s | 1075 m | Lactate |
| | 1060 w | | |
| 1035 s | 1030 s | 1035 s | Lactate |
| 980 sh | 1000 w | 1000 w | |
| 925 w | 920 m | 925 m | Lactate |
| | | 880 w | |
| 860 m | 850 s | 850 s | |
| 840 sh | | | |
| | | 800 sh | |
| 760 w | 750 m | 760 m | |
| | 640 w | 680 w | |
| 625 w | 620 m | 620 m | |
| | | 580 m | |
| 525 w | 520 w | | $\nu$Pt-N |
| | 500 w | 480 m | |
| 440 w | 430 w | 440 m | $\nu$Pt-O? |
| | 410 w | | |

[a]Spectra run as nujol mulls. Abbreviations: s = strong; m = medium; w = weak; sh = shoulder.

EXAMPLE 4

Evaluation of Anti-Tumor Activity

The compounds were evaluated for anti-tumor activity against S180 ascites in female CFW Swiss mice by the following procedure:

CFW mice, averaging 20 g, are immediately inspected and placed in newly prepared cages. On day zero the mice are inoculated with 0.2 ml of a freshly prepared saline suspension (0.15 M NaCl) containing $1 \times 10^7$ tumor cells/ml, or a total of $2 \times 10^6$ cells. This inoculum is freshly prepared using "transfer" mice which have been injected with tumor cells the previous week. This inoculum is the end-product of a series of steps which involves (1) the removal of the cells from the peritoneal cavity of the sacrificed transfer mouse, (2) alternate centrifugation-washing (2-3 times with cold saline) to remove occasional blood and other undesirable components, and finally (3) dilution (1:3) of the packed cell volume with saline (the final centrifugation being carried out at 1,000 rpm for 2 min.). A cell count is made on a 2,000-fold dilution of this 1:3 suspension by means of a Coulter Counter. A final dilution to $1 \times 10^7$ cells/ml is made based on the averaged count. On day 1, solutions of the test compounds are prepared and the mice injected, with each mouse of a set of four mice being injected with the same test compound at the same dose level.

Also, on this day, two types of controls (6 mice/set) are employed: (1) Normal (1 set): 0.5 ml of the solvent medium used for the test compound, and (2) Positive control (1 set): a known anti-tumor agent cis-[Pt(NH$_3$)$_2$Cl$_2$] in saline at 8 mg/kg), used to test the response of the biological system.

The effectiveness of a compound is measured in terms of the increase in life span of the test animals relative to the controls (calculated from the day of tumor inoculation (day zero). In order to standardize the test data and permit intercomparisons to be made, the day of evaluation is arbitrarily taken as that day corresponding to twice the mean life-span (or average day of death) of the normal controls. This sets a practical upper limit of 100% on the ILS attainable. For calculation purposes, survivors on the day of evalution are considered to have died on that day. The % ILS is formulated as:

$$\%ILS = \left( \frac{\text{mean life-span of test mice}}{\text{mean life-span of control mice}} - 1 \right) \times 100\%$$

ILS values above 50% represent significant activity; those above 75% represent excellent activity.

Anti-tumor screening results for cis-[PtA$_2$(lactate)$_2$] are summarized in Table II.

TABLE II

Anti-Tumor Screening Data for cis-[PtA$_2$(C$_3$H$_5$O$_3$)$_2$] vs. the S180 Ascites Tumor System

| Compound | Medium | Dose (mg/kg)$^a$ | % ILS | 30-Day Survivors | % ILS$^b$ | Positive Control 30-Day Survivors |
|---|---|---|---|---|---|---|
| Example 1 (A=NH$_3$) | Water | 15 | 100 | 4/4 | 77 | 3/6 |
| | | 30 | 100 | 4/4 | | |
| | | 60 | −66 | 0/4 | | |
| | | 120 | −76 | 0/4 | | |
| Example 2 (A=CH$_3$NH$_2$) | Water | 15 | 47 | 0/4 | 78 | 2/6 |
| | | 30 | 50 | 2/4 | | |
| | | 60 | 76 | 1/3 | | |
| | | 120 | 100 | 2/4 | | |
| Example 3 (A=en) | Water | 20 | 100 | 4/4 | 81 | 3/6 |
| | | 40 | 100 | 4/4 | | |
| | | 80 | 63 | 3/4 | | |
| | | 160 | −71 | 0/4 | | |

$^a$4 mice/dose
$^b$Positive control = 8 mg/kg cis-[Pt(NH$_3$)$_2$Cl$_2$] in saline.

All compounds were administered as aqueous solutions. All show excellent activity against this tumor system, but at different dose levels.

Cis-[Pt(NH$_3$)$_2$(lactate)$_2$] is highly active at 15 and 30 mg/kg and is toxic at 60 mg/kg.

Cis-[Pt(CH$_3$NH$_2$)$_2$(lactate)$_2$] is considerably less potent as an anti-tumor agent than the NH$_3$ analog, with a threshold of activity at ca. 30 mg/kg and excellent activity at 120 mg/kg. The toxic level was not reached.

[Pt(en)(lactate)$_2$] is highly active at 20 and 40 mg/kg and toxic at 160 mg/kg.

Ridgway et al., in the "Proceedings of the Third International Symposium on Platinum Coordination Complexes in Cancer Chemotherapy" held in October 1976, at the Wadley Institute and reported in J. of Clinical Hematology and Oncology, 7, No. 1, p. 225 and No. 3, p. 856 (1977) listed the lactate complex of diaminocyclohexane platinum(II), cis-[Pt(DACHXN) (lactate)$_2$], and gave an M (figure or merit) of 22 against Leukemia L1210 for this compound against 3.3 for cis-[Pt(NH$_3$)$_2$Cl$_2$]; where, $$M = \frac{LD_{50} \times \text{Best } \%ILS}{ID_{99.9} \times 100}$$

When the cis-[Pt(DACHXN) (lactate)$_2$] of the prior art was tested along with the platinum lactate complexes of the present invention for comparison purposes, it was found to be most active at 25 mg/kg and toxic at 100 mg/kg.

In the above publication, no solubility data was given. Cis-[Pt(DACHXN) (lactate)$_2$] prepared according to the process of this invention was less soluble in water than 0.1 g/100 ml, which is much less than the solubilities of the platinum amine lactate complexes of this invention (greater than 10 g/100 ml of water when freshly prepared). Low water solubility greatly reduces the utility of the compound for oral or intravenous administration.

If the active and toxic doses observed for these compounds are "normalized" in terms of platinum content of each compound, wide differences in active and toxic doses are still observed. Differences in platinum content resulting from different amine ligands do not explain differences in active and toxic doses.

Cis-[Pt(NH$_3$)$_2$(lactate)$_2$] was also tested vs. L1210 lymphoid leukemia in mice through the National Cancer Institute. The results of this test are summarized in Table III.

TABLE III

Anti-Tumor Screening Results vs. the L1210 Tumor System

| Compound | Dose Regimen$^a$ | Dose (mg/kg) | T/C$^b$ | Toxicity Day Survivors$^d$ |
|---|---|---|---|---|
| Cis-[Pt(NH$_3$)$_2$(lactate)$_2$] | Day 1, 5, 9 | 120 | T$^c$ | 2/6 |
| | | 60 | 114 | 6/6 |
| | | 30 | 138 | 6/6 |
| | | 15 | 108 | 6/6 |
| | | 7.5 | 100 | 6/6 |

$^a$Day 1, 5, 9 = Doses administered on Days 1, 5 and 9.
$^b$T/C = [Mean life span (test)/Mean life span (control)] × 100
$^c$T = Toxic by NCI criteria (Geran, et al. "Protocols for screening Chemical Agents and Natural Products Against Animal Tumors and Other Biological Systems." Cancer Chemotherapy Reports, Part 3, 3rd. ed., Summer, 1972)
$^d$Number of survivors on Day 5.

The compound showed peak activity at 30 mg/kg (T/C-138), in agreement with the S180a results. By comparison, the NCI's cis-[Pt(NH$_3$)$_2$Cl$_2$] positive control showed a maximum T/C of 152 at 5.0 mg/kg using the Day 1, 5 and 9 dose regimen.

What is claimed is:

1. A complex of the general formula:

cis-[Pt(II)A$_2$(C$_3$H$_5$O$_3$)$_2$]

wherein the platinum, Pt, is in valence state II and is coordinated to A in a cis configuration; A is ammonia or a monodenate alkylamine; A$_2$ is a bidentate alkylamine; and C$_3$H$_5$O$_3$ is the lactate anion.

2. A complex according to claim 1 wherein A is represented by formula RNH$_2$, and R is hydrogen or lower alkyl.

3. A complex according to claim 2 wherein R is hydrogen.

4. A complex according to claim 2 wherein R is a lower alkyl.

5. A complex according to claim 4 wherein R is methyl.

6. A complex according to claim 4 wherein A is represented by the formula:
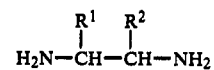
wherein each of $R^1$ and $R^2$ is hydrogen or lower alkyl.
7. A complex according to claim 6 wherein each of $R^1$ and $R^2$ is hydrogen.
* * * * *